(12) United States Patent
Workman, Jr.

(10) Patent No.: US 6,452,679 B1
(45) Date of Patent: Sep. 17, 2002

(54) METHOD AND APPARATUS FOR CONTROLLING THE MANUFACTURING QUALITY OF A MOVING WEB

(75) Inventor: Jerome J. Workman, Jr., Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/474,720

(22) Filed: Dec. 29, 1999

(51) Int. Cl.[7] .............................................. G01N 21/84
(52) U.S. Cl. ................................. 356/429; 250/339.02
(58) Field of Search ............................... 358/429, 430, 358/431, 435; 250/339.02

(56) References Cited

U.S. PATENT DOCUMENTS

| | | |
|---|---|---|
| 3,981,758 A | 9/1976 | Thayer et al. |
| 3,992,107 A | 11/1976 | Loy |
| 4,031,752 A | 6/1977 | Sanders |
| 4,084,896 A | 4/1978 | Warter, Jr. et al. |
| 4,097,743 A | 6/1978 | Carlson |
| 4,186,309 A | 1/1980 | Gnuechtel |
| 4,377,238 A | 3/1983 | Wilks et al. |

(List continued on next page.)

FOREIGN PATENT DOCUMENTS

| | | |
|---|---|---|
| DE | 196 53 477 A1 | 6/1998 |
| DE | 197 09 963 A1 | 9/1998 |
| DE | 198 30 323 A1 | 1/1999 |
| EP | 0 681 183 A2 | 11/1995 |
| WO | WO 98/28490 | 7/1998 |
| WO | WO/98/40727 | 9/1998 |
| WO | WO/99/02941 | 1/1999 |

OTHER PUBLICATIONS

Article entitled "Quantification of LDPE [Low Density Poly(ethylene)], LLDPE [Linear Low Density Poly(ethylene)] in Polymer Film Mixtures "as Received" Using Multivariate Modeling with Data Augmentation (Data Fusion) and Infrared, Raman, and Near–Infrared Spectroscopy," *Sprectroscopy Letters*, 32(6), 1057–1071 (1999).
International Search Report for application No: PCT/US00/34636 dated Jun. 6, 2001
Jerome J. Workman, "A Review of Process Near Infrared Spectroscopy," *J. Near Infrared Spectrosc.* 1, 221–245 (1993).
Jerome J. Workman, "NIR–MIR Non–Contact Measurement and Imaging Systems for Solid Samples," *NIR News* 8(5), 13–15 (1997) (reprinted).
Jerome J. Workman, "Applications for NIR–MIR Non–Contact Measurement and Imaging Systems," *NIR News* 8(6) (reprinted).
Jerome J. Workman, "Interpretive Spectroscopy for Near–Infrared," *Appl. Spectrosc. Rev.* 31(3), 251 (1996).

*Primary Examiner*—Frank G. Font
*Assistant Examiner*—Layla Lauchman
(74) *Attorney, Agent, or Firm*—Nelson Mullins Riley & Scarborough

(57) ABSTRACT

A method and apparatus for detecting the composition of a moving web product on a real-time basis during the manufacturing process. Spectrometric monitoring equipment operates to derive information regarding physical and/or chemical properties of the web at multiple locations in the web's cross direction. Data from a plurality of spectral regions can be combined to produce a vector containing accurate information regarding the web's composition. This information is derived using multivariate mathematical techniques to yield a spatial data matrix for each component of interest. Composition information contained in the spatial data matrix can be reprojected as a "virtual composition map," or compared against ideal profiles stored in a computer memory.

33 Claims, 5 Drawing Sheets

U.S. PATENT DOCUMENTS

| | | |
|---|---|---|
| 4,543,157 A | 9/1985 | Jones et al. |
| 4,592,318 A | 6/1986 | Pouring |
| 4,742,772 A | 5/1988 | Grose |
| 4,775,238 A | 10/1988 | Weber |
| 4,781,880 A | 11/1988 | Robbins, III |
| 4,828,156 A | 5/1989 | Whiteley et al. |
| 4,835,720 A | 5/1989 | Ditto et al. |
| 4,866,288 A | 9/1989 | Weber |
| 4,928,013 A | 5/1990 | Howarth et al. |
| 5,023,815 A | 6/1991 | Wilson et al. |
| 5,116,625 A | 5/1992 | Patel et al. |
| 5,122,232 A | 6/1992 | Lyman et al. |
| 5,124,552 A | 6/1992 | Anderson |
| 5,244,518 A | 9/1993 | Krayenhagen et al. |
| 5,411,648 A | 5/1995 | Houlachi et al. |
| 5,466,159 A | 11/1995 | Clark et al. |
| 5,491,340 A | 2/1996 | Saarinen |
| 5,504,979 A | 4/1996 | Sheehan et al. |
| 5,515,585 A | 5/1996 | Sheehan et al. |
| 5,563,809 A | 10/1996 | Williams et al. ............ 364/560 |
| 5,596,412 A | 1/1997 | Lex |
| 5,603,806 A | 2/1997 | Kerttula |
| 5,656,124 A | 8/1997 | Krayenhagen et al. |
| 5,718,060 A | 2/1998 | Mori |
| 5,735,694 A | 4/1998 | Clark et al. |
| 5,740,593 A | 4/1998 | Sheehan et al. |
| 5,745,365 A | 4/1998 | Parker |
| 5,756,156 A | 5/1998 | Elijoki et al. |
| 5,777,621 A | 7/1998 | Schneider et al. |
| 5,799,242 A | 8/1998 | Sano |
| 5,822,070 A | * 10/1998 | Syre ......................... 356/419 |
| 5,827,196 A | 10/1998 | Yeo et al. |
| 5,838,158 A | 11/1998 | Beck et al. |
| 5,858,890 A | 1/1999 | Sheehan et al. |
| 5,895,470 A | 4/1999 | Pirolli et al. |
| 5,908,792 A | 6/1999 | Sheehan et al. |
| 5,926,180 A | 7/1999 | Shimamura |
| 5,944,957 A | 8/1999 | Fagerlund et al. |
| 5,964,980 A | 10/1999 | Robinett |

* cited by examiner

METHOD AND APPARATUS FOR CONTROLLING THE MANUFACTURING QUALITY OF A MOVING WEB

BACKGROUND OF THE INVENTION

The present invention relates to techniques for monitoring and controlling the manufacture of a moving web of product, such as a web of tissue product. More particularly, the present invention relates to an apparatus and method that provides composition information regarding the moving web which can be used to control the manufacturing process.

Modern facilities for the production of facial tissue and other fibrous webs can operate at line speeds in excess of 2000 feet/minute. As the web progresses through the manufacturing process, various substances are often applied to impart certain desirable characteristics to the final product. For example, tissue product may be impregnated with a relatively "heavy" add-on, such as a skin lotion or moisturizer. Other substances, such as analgesics or other over-the-counter medications, may also be applied in some cases.

Information regarding the composition of the web product has been obtained in the past using "off-line" analysis. Specifically, a sample of the product has simply been removed from the web and analyzed in a laboratory for its constituent components. For example, a "mass balance" analysis has often been used to determine the concentration of lotion applied to facial tissue. According to this technique, the substance in question is removed from the sample by extraction. Weighing the sample both before and after the extraction yields the weight, and thus the concentration, of the lotion.

Compositional information derived by off-line analysis is of little use in making instantaneous adjustments to the manufacturing process. Due to the line speeds at which the web product moves, application of excess quantities of lotion or another such substance can quickly become costly. In addition, a pure mass balance analysis provides no information regarding the concentration of the substance of interest at various locations across the web's surface. Furthermore, mass balance is often inadequate to determine concentration of "lighter" add-ons such as medications.

SUMMARY OF THE INVENTION

The present invention recognizes and addresses the foregoing disadvantages, and others, of the prior art. Accordingly, it is an object of the present invention to provide reliable information regarding the composition of a moving web on a real-time basis.

It is a further object of the present invention to simultaneously provide composition information in relation to multiple aspects of a moving web for purposes of process control or quality analysis.

It is a more particular object of the present invention to provide a graphical display of composition information regarding the make-up of a moving web.

It is a further object of the present invention to provide various improvements in the manufacture of paper tissue product.

Some of these objects are achieved by a real-time method of deriving composition information regarding a moving web in a manufacturing environment. According to the method, a photodetector assembly is provided having a plurality of photodetectors at respective detection locations across the transverse direction of the moving web. The moving web is then illuminated so as to provide electromagnetic energy at each of the photodetectors. At least two selected frequencies of electromagnetic energy are then measured at each of the detection locations. Finally, the composition information for each detection location is derived based on absorbance of electromagnetic energy thereat.

Exemplary methodology further comprises the step of controlling application of the predetermined component to the moving web based on the derived composition information. For example, application of the predetermined component may be controlled automatically based on the composition information. Alternatively, or in addition, a graphical display can be presented to a human operator showing quantitative levels of the predetermined component in a cross direction of the moving web. In such cases, application of the predetermined component can be manually controlled by the human operator.

Where a graphical display is produced, the graphical display can illustrate quantitative levels correlated to a two- or three-dimensional representation of the moving web. A two- or three-dimensional representation is preferred as it yields a graphical display which takes advantage of the human operator's natural pattern recognition skills. Preferably, the graphical display will show quantitative levels of the predetermined component in both cross and machine directions.

Other objects of the present invention are achieved by an apparatus for deriving composition information regarding at least one predetermined component of a moving web. The apparatus comprises a plurality of radiation sources adapted to illuminate the web with electromagnetic energy in at least two predetermined frequency bands. The apparatus further includes a photodetector assembly having a plurality of photodetectors spaced apart from the moving web for detecting levels of electromagnetic energy in the respective frequency bands. In addition, electromagnetic energy levels are detected at multiple detection locations across the transverse direction of the moving web. Processor means in electrical communication with the photodetector assembly are also provided. The processor means are operative to derive composition information for each detection location based on absorbance of electromagnetic energy thereat.

In exemplary embodiments, the apparatus may further comprise display means for presenting a graphical display showing quantitative levels of the predetermined component in a cross direction of the moving web. Preferably, the display means may be operative to present the quantitative levels correlated to a two- or three-dimensional representation of the moving web to advantageously utilize the pattern recognition skills of the human operator. The display means may also be configured to further show quantitative levels in a machine direction of the moving web.

In some embodiments, the plurality of radiation sources may be situated on a same side of the moving web as the photodetector assembly. In other embodiments, the plurality of radiation sources may be situated on an opposite side of the moving web from the photodetector assembly. Of course, the radiation sources may be placed on both sides of the moving web in some cases.

Other objects of the present invention are achieved by a real-time method of deriving composition information regarding at least one predetermined component added to a moving web of tissue paper in a manufacturing environment. According to the method, the moving web is illuminated with electromagnetic energy in at least two predetermined frequency bands. Next, electromagnetic energy as diffused by the moving web is measured at each of a plurality of detection locations across a transverse direction thereof. Composition information for each of the detection locations is derived based on absorbance of electromagnetic energy thereat. Finally, application of the predetermined component to the moving web is controlled based on the component information.

Additional objects of the present invention are achieved by a realtime method of deriving composition information regarding at least one predetermined component added to a moving web. One step of the method involves illuminating the moving web with electromagnetic energy. At each of a plurality of detection locations across a transverse direction of the moving web, electromagnetic energy is measured in a plurality of frequency bands falling within a frequency range of 0.2–200 microns. The spectral information from the frequency bands is then combined into a supervector. An additional step involves processing the supervector using multivariate mathematical techniques to produce a spatial data matrix of the composition information as correlated to the detection locations.

Other objects, features and aspects of the present invention are achieved by various combinations and subcombinations of the disclosed elements, which are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which.

Figure 1:
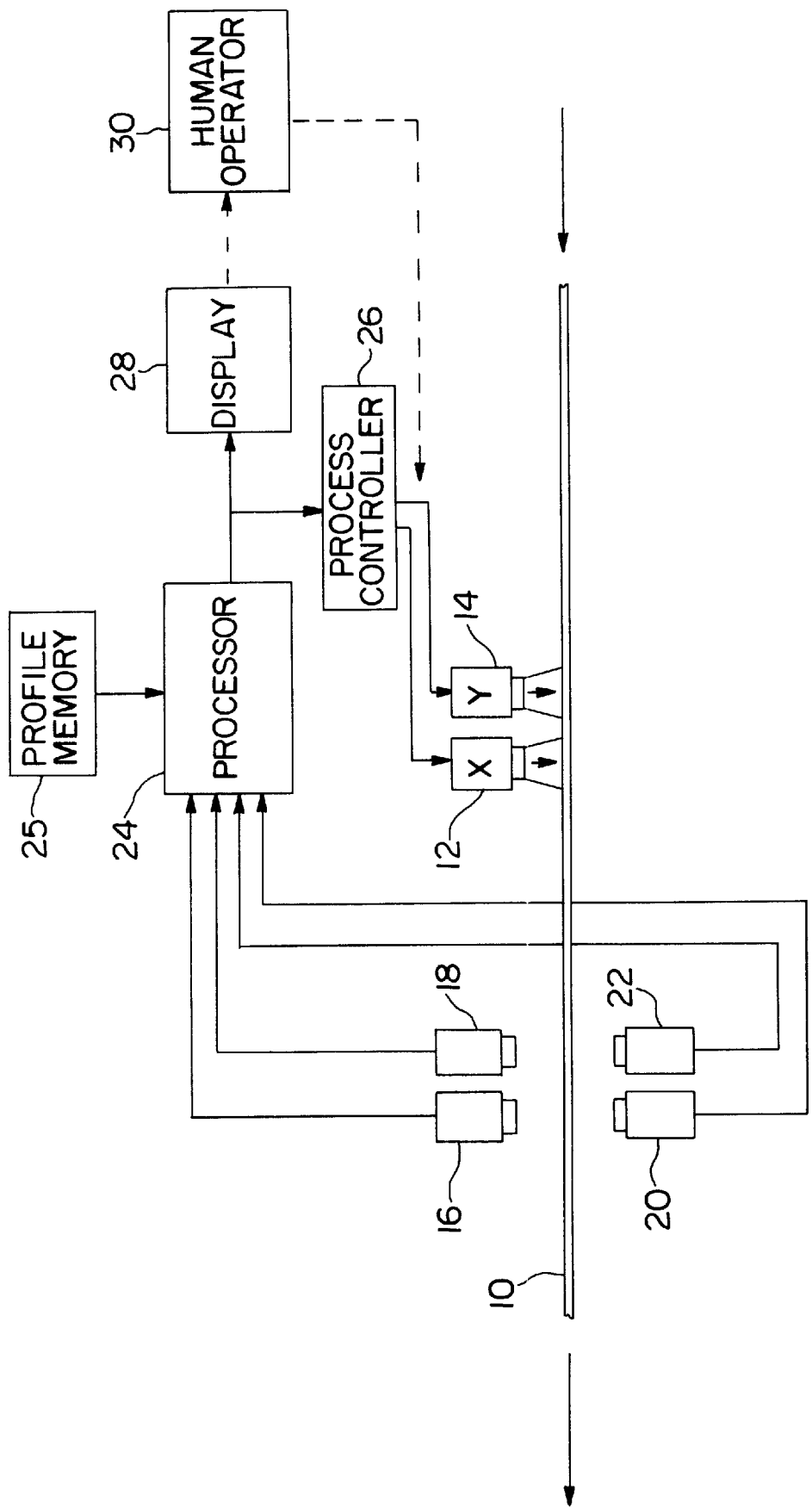
FIG. 1 is a diagrammatic representation of a system constructed in accordance with the present invention for ascertaining composition information regarding a moving web.

Repeat use of reference characters in the present specification and drawings is intended to represent same or analogous features or elements of the invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary constructions.

In accordance with the present invention, it has been found that composition information regarding a moving web product can be accurately derived using specially-adapted spectrometric monitoring equipment. For example, information regarding the concentration of substances added during the manufacturing process can be determined at several locations in the cross direction of the moving web. This information can be used in digital form to automatically control upstream parameters in the manufacturing process. A graphical display can also be presented to a human operator to illustrate the web's composition on a real time basis. In addition, information regarding various physical properties of the web (such as thickness, density, opacity and the like) can also be obtained for quality control purposes.

FIG. 1 illustrates a moving web 10 progressing through a manufacturing process at typical line speeds. Sprayers 12 and 14 continuously apply respective components "X" and "Y" to the passing surface of moving web 10. In the case of facial tissue, for example, component X may often be a lotion or moisturizing formulation. Component Y may be a "minor" component such as an over-the-counter medication, applied to the web in significantly lower concentrations than component X.

In this case, a pair of spectrometric assemblies 16 and 18 are located above moving web 10. A pair of spectrometic assemblies 20 and 22 are likewise located below moving web 10, as shown. The spectrometric devices operate to measure absorbance of electromagnetic energy at selected frequencies in the spectrum of electromagnetic radiation. As will be explained more fully below, the measurements taken by the spectrometric devices are fed to a processor 24, which applies multivariate mathematical techniques to derive the desired composition information.

A suitable memory means 25, associated with processor 24, stores information regarding the ideal values of each component or other such property being measured. As such, processor 24 can compare the derived information with a desired profile for that attribute of the web. Composition information is fed to a process controller 26 for automatic control of sprayers 12 and 14, or other controllable manufacturing parameters. Alternatively, or in addition, the composition information may be fed to a display 28, such as a suitable flat panel or CRT. Responding to the display, a human operator 30 can also control various aspects of the manufacturing process. A two- or three-dimensional graphical display is preferred in order to take advantage of the operator's natural pattern recognition skills.

The spectrometric assemblies in the system of FIG. 1 use selected frequency bands to reveal detailed information about the composition of moving web 10. In this regard, it is helpful to review some general aspects of spectrometric theory before discussing further details of the invention. The first assumption in spectroscopic measurement is that Beer's Law relationship applies between a change in spectrometer response and the concentration of analyte material present in a sample specimen. The Bouguer, Lambert and Beer relationship assumes that the transmission (or reflectance) of a sample within an incident beam is equivalent to 10 exponent the negative product of the molar extinction coefficient (in $L \cdot mol^{-1} cm^{-1}$), times the concentration of a molecule in solution (in $mol^{-1} L^{-1}$) times the pathlength (in cm) of the sample in solution. The Bouguer, Lambert and Beer (Beer's law) relationship is given as:

$$T = \frac{I}{I_o} = \exp(-\varepsilon c l)$$

where T=transmittance, $I_o$=intensity of incident energy, I=intensity of transmitted light, $\varepsilon$=molar extinction coefficient (in $L \cdot mol^{-1} cm^{-1}$), C=concentration (in $mol \cdot L^{-1}$), and L=pathlength (in cm).

The above equation may be simplified into its more standard form showing absorbance as a logarithmic term, used to linearize the relationship between spectrophotometer response and concentration. This gives the expression below as the relationship between absorbance and concentration:

$$\text{Abs.} = A = -\log\left(\frac{I}{I_o}\right) = -\log(T) = \varepsilon c l$$

Note: the reflectance (R) term can be substituted for the transmittance (T) term for a Lambertian infinitely thick reflector.

The following statements hold true for what is most often termed Beer's Law: (1) The relationship between transmittance (or reflectance) and concentration is nonlinear, (2) yet the relationship between absorbance and concentration is linear. A further explanation of the physics of spectrometry can be found in J. Workman, Jr., "A Review of Process Near Infrared Spectroscopy: 1980–1994," *Journal of Near Infrared Spectroscopy* 1, 221–245 (1993), incorporated herein by reference.

Thus, Beer's Law can be used to derive composition information regarding the concentration of a component in a moving web. Spectra measurements may be taken in a bulk transmission mode in which the radiation source and detector are located on opposite sides of the moving web. Alternatively, measurements may be taken in a diffuse reflectance mode in which the source and detector are located on the same side of the web. Bulk transmission measurements can be made to detect total add-on levels for the entire sample, whereas measurement of the add-on levels for each surface typically requires the use of diffuse reflectance.

In accordance with the present invention, multiple regions of the electromagnetic spectrum are selected to contain the most reliable information about each of the components or other properties of interest. Richer composition information can be obtained if multiple spectral regions are simultaneously detected rather than merely detecting composition information using a single region. The various spectral regions (e.g., ultraviolet+visible+near infrared (NIR)+ infrared (IR)+Raman, etc.), each containing some information regarding the attribute in question, can be simultaneously detected and combined into a single "supervector" using spectral fusion. The supervector is then processed using multivariate data analysis to produce a spatial data matrix of the required properties correlated to the detection locations. Typically, the spectral regions will fall in the wavelength range of 0.2–200 microns.

In this regard, each set of specific sources and detectors is preferably optimized for a specific measurement region. Each detector can then be moved over the surface of the web (rastered), or the detectors can be set up in multiple sensor arrays. In this latter case, each of the arrays would typically be configured for a specific type of wavelength measurement (e.g., one for ultraviolet, visible, NIR, IR or Raman). Thus, each of the spectrometric assemblies 16, 18, 20 and 22 shown in the example of FIG. 1 will be configured for detection of radiation in a selected region of the electromagnetic spectrum.

Typically, the minimum number of frequency measurements required for a property determination would be at least two, one for measurement and one for reference frequencies. The measurement of at least one reference wavelength and one property wavelength is desirable to compensate for baseline changes which also affect the overall measurement signal for the property of interest. The need to measure two such frequencies is exacerbated by the motion of a web system and the variability of signal based on web flutter and surface conditions. In contrast, a single frequency may give rise to less stable results as there is no reference point to use for signal correction.

Figure 2:
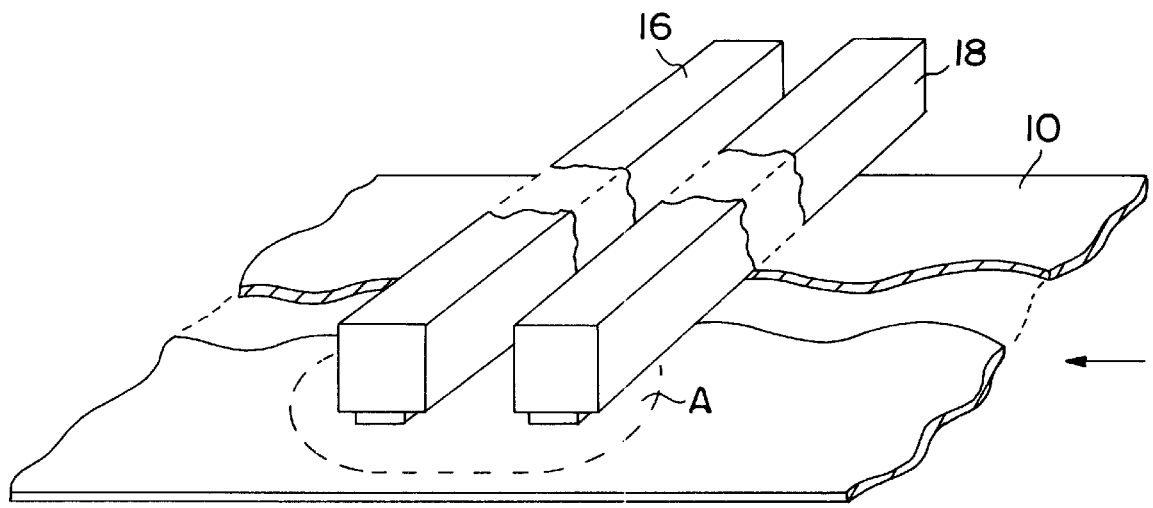
FIG. 2 is a perspective view showing a plurality of spectrometric assemblies situated over the path of the moving web.
Figure 3:
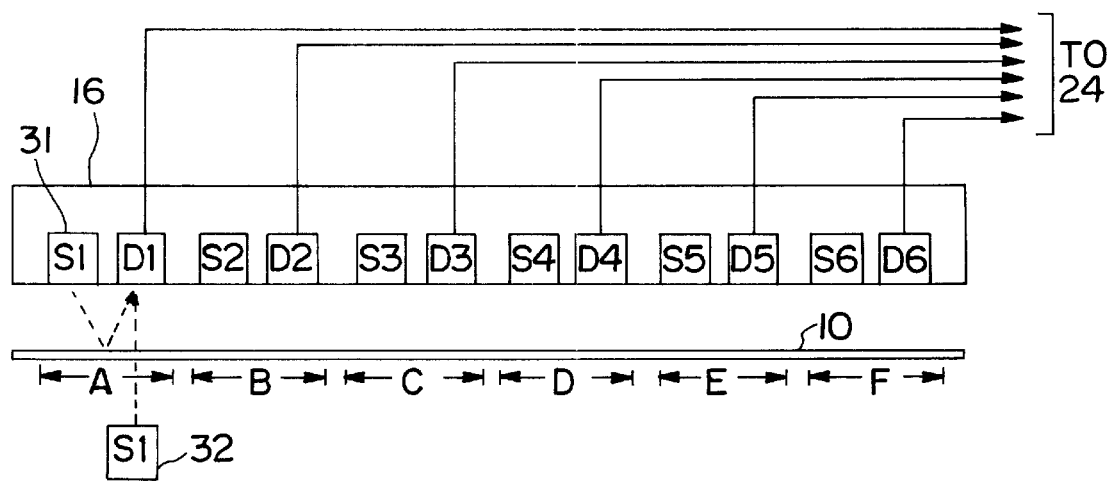
FIG. 3 is a diagrammatic representation showing the relative positions of multiple radiation sources and spectrometric detectors in each of the assemblies illustrated in FIG. 2.

Referring now to FIGS. 2 and 3, each of the spectrometric devices is constructed in this case having a plurality of fixed photodetectors located adjacent respective detection locations A–F in the transverse (or "cross") direction of the moving web. This arrangement eliminates the need for a traversing detector, which results in some loss of information because the web itself is moving as the detector traverses. As shown in FIG. 3, for example, assembly 16 includes a plurality of fixed photodetectors D1–D6.

One or more radiation sources (S1–S6) are respectively associated with each of the photodetectors. For example, two radiation sources are associated with each of the detectors in the illustrated embodiment. Using detector D1 as an example, the first such source (indicated by the reference number 31) is located on the same side of web 10 as the detector in order to obtain diffuse reflectance measurements. The second such source 32 directs incident radiation through web 10 for bulk transmission measurement. Where diffuse reflectance measurements are to be taken, the source and its associated detector will often be located in a common enclosure. Where bulk transmission measurements are to be taken, the source and detector will typically be located in separate enclosures located on opposite sides of moving web 10.

As noted above, the signal outputs of the photodetectors are fed to processor 24 for further analysis. While processor 24 is shown as a single device in FIG. 1, it should be understood that various functions of the data processing procedure can be distributed among several computational devices. For example, commercial spectrometers are often provided with an electronic control unit (ECU) in which at least some preprocessing of the data takes place. This data may then be fed to a specially programmed computer for further processing, as well as for generation of desired graphical displays.

While various types of spectrometric devices may be utilized within the teachings of the present invention, presently preferred embodiments employ filter spectrometers to derive the composition information. Generally speaking, filter spectrometers produce an indication of absorbance in selected frequency bands by comparing reference and measured values of radiation appearing in that band. The reference value is typically obtained by directing electromagnetic energy from the radiation source directly to the detector. The measured value is electromagnetic energy collected after interaction with the sample material. The frequency of interest is typically produced by passing broadband radiation from the radiation source through one or more narrow band filters. The construction of a filter spectrometer which can be adapted for use in the present invention is described in U.S. Pat. No. 4,097,743 to Carlson, incorporated herein by reference.

Figure 4:
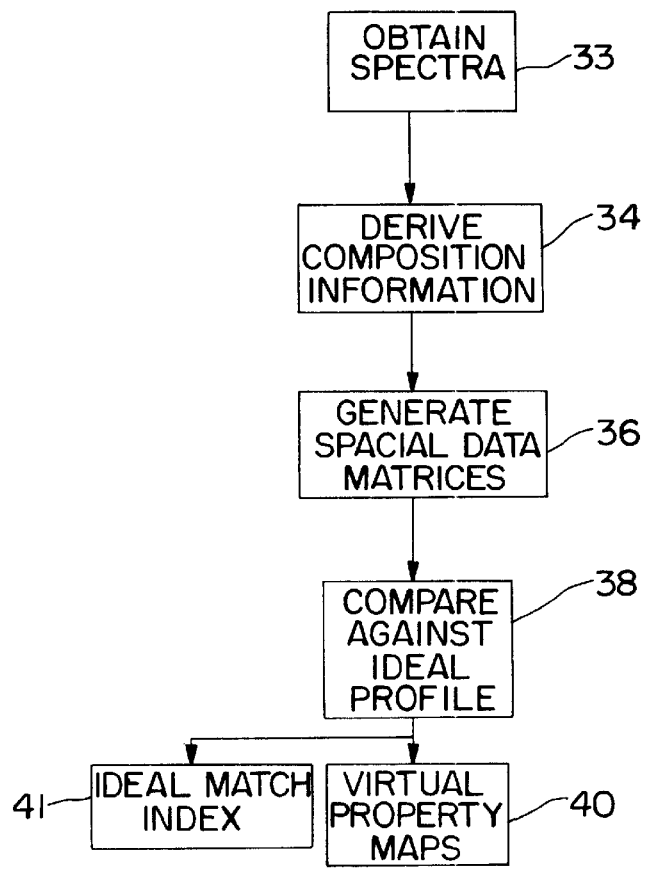
FIG. 4 is a flowchart of general method steps used to derive composition information in the system of FIG. 1.

FIG. 4 illustrates the general process steps utilized to derive the component information in the system of FIG. 1. At block 33, electromagnetic energy at selected frequencies is detected at each of the detection locations in the cross direction of the web. Preferably, the multiple spectra are combined by spectral fusion to generate the "supervector" from which component data will be produced. This occurs at block 34, where multivariate full-spectral chemometrics are applied to calculate a spatial data matrix of the required properties. (Actually, a number of spatial data matrices may be derived from the same spectral supervector information.)

It is contemplated that the spatial data matrices may be "reprojected" using graphical techniques to produce a virtual property map (i.e., composition map) of the component in question. As an alternative to direct projection, the profile may be compared to an ideal profile for each web property of interest (as indicated at block 38). Going now to block 40, the resulting deviation maps may be displayed to a human operator for visual interpretation, or may be subjected to image analysis or pattern recognition for automated control. As indicated at 41, the ideal match index for the actual versus ideal could also be calculated as a single integer number representing the "alikeness" or Simple Quality Value for the component of interest during the web manufacturing process.

Figure 5:
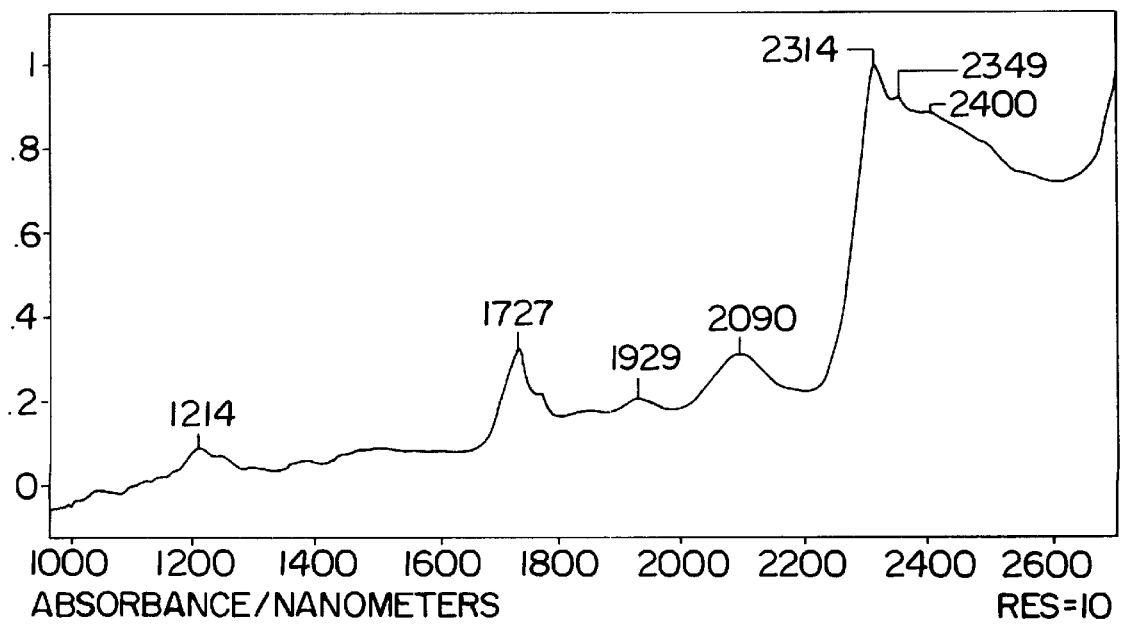
FIG. 5 is an exemplary spectrum from which some composition information can be derived.

FIG. 5 illustrates an example of one spectrum that may be used to obtain information regarding the quantity of lotion applied to facial tissue. In this example, the spectrum represents the difference between a spectrum of untreated tissue and a spectrum of tissue to which the lotion had been applied. The spectrums were obtained by bulk transmission of NIR electromagnetic energy.

As can be seen, the resulting spectrum exhibits multiple absorbance peaks, some of which correspond to the lotion material on the treated tissue. For example, peaks at 1214 nm, 1727 nm, 2314 nm and 2400 nm indicate the presence of mineral oil, a major constituent of the lotion. Mathematical processing of these absorbance values thus gives an indication of lotion concentration at a particular detection location.

Figure 6:
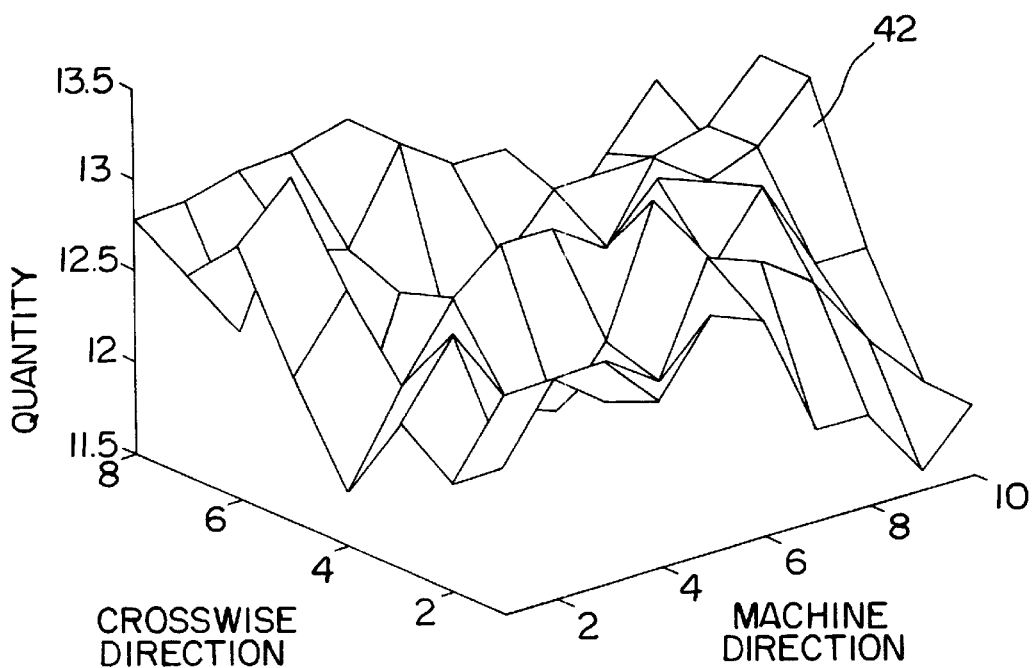
FIG. 6 is an exemplary three-dimensional composition map that may be displayed based on the derived composition information.

The remaining figures illustrate various graphical displays that can be generated with the composition information. For example, FIG. 6 shows a three-dimensional mesh image 42 of add-on percentages for a particular component of interest, at each of the detection locations. The resulting map shows the add-on percentages correlated to the surface of the web in a manner that is easily recognizable by a human operator. In this case, the map shows concentration levels in the machine direction on a first in-first out basis that gives the appearance of movement corresponding to movement of the web product.

Figure 7:
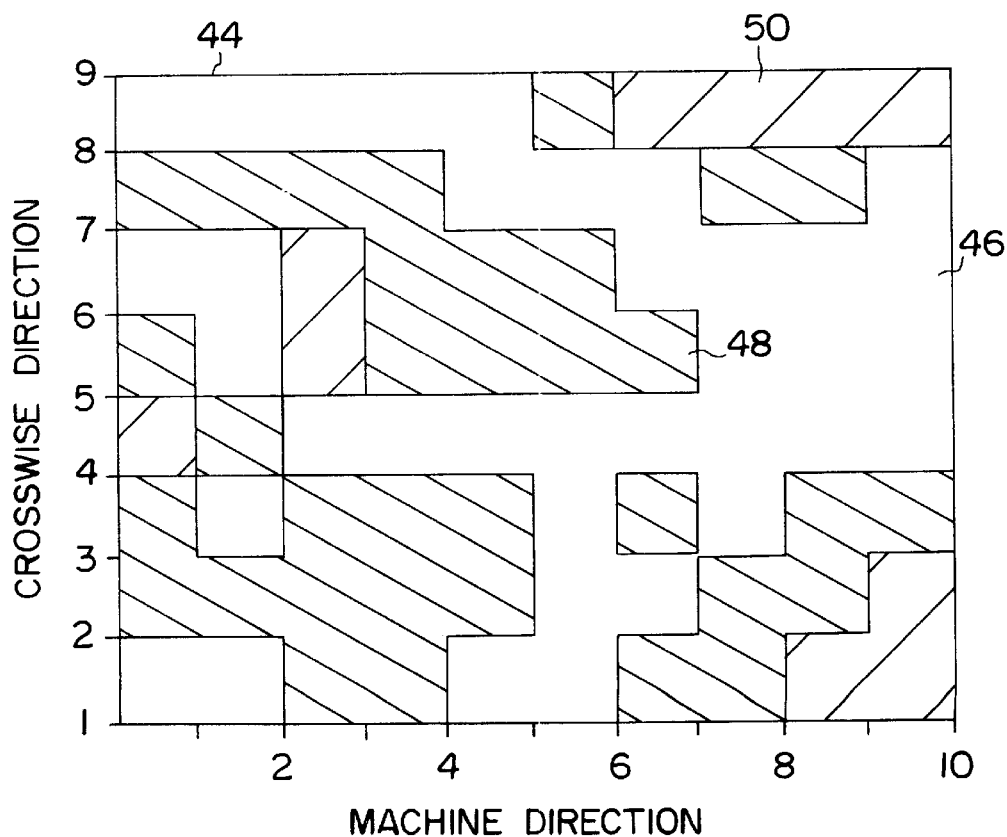
FIG. 7 is an exemplary two-dimensional composition map that may be displayed based on the derived composition information.

FIG. 7 illustrates a two-dimensional representation of the same data. In this case, regions of high, medium or low add-on percentages are indicated by a respective color. Thus, high levels of add-on are indicated by a first color, which may simply be white. Medium add-on levels near the target value may be represented by a second color 48. A third color 50 designates lower levels of add-on for the component of interest.

Figure 8A:
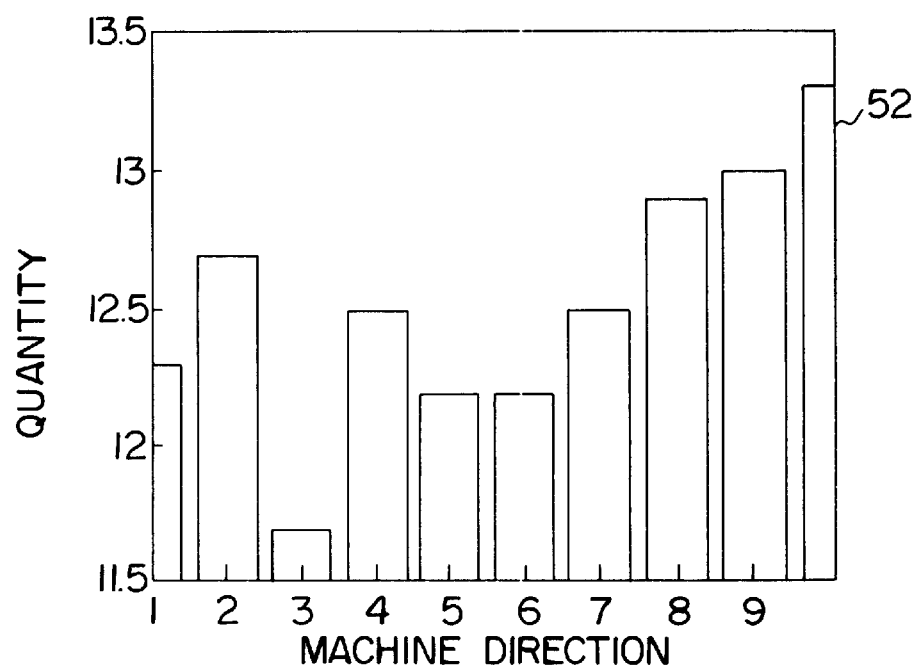
FIGS. 8A and 8B are bar graph displays in the machine direction and cross direction, respectively, that may be presented based on the derived composition information.
Figure 8B:
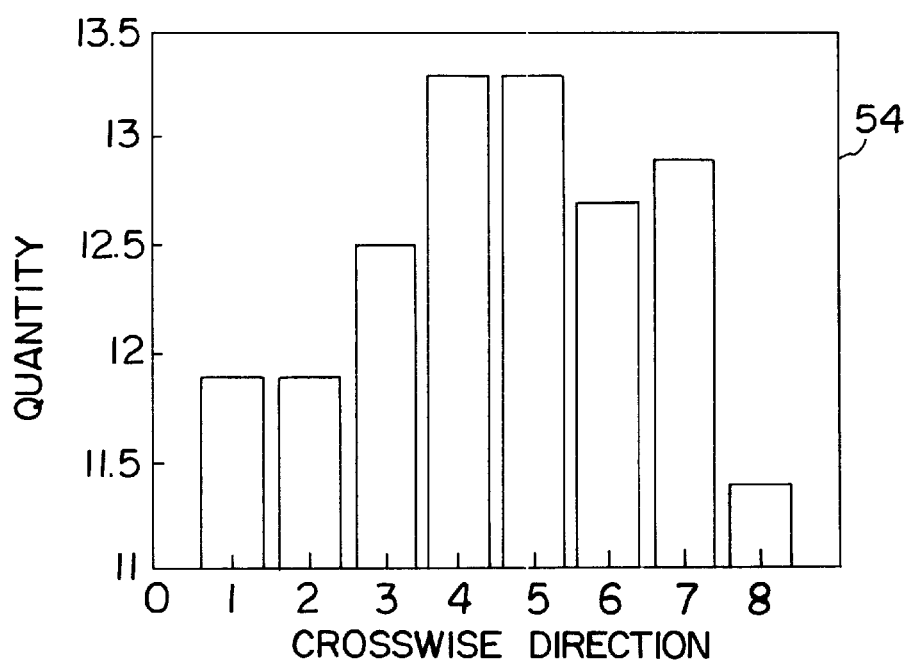

A still further type of graphical display is illustrated in FIGS. 8A and 8B. Specifically, FIG. 8A shows a bar graph 52 in which composition information is displayed on a first in-first out basis in the machine direction of the web. Composition information in the crosswise direction of the moving web at the various detection locations is shown by bar graph 54 of FIG. 8B.

It can thus be seen that the present invention provides an improved method and apparatus for controlling the manufacturing quality of a moving web. While preferred embodiments of the invention have been shown and described, modifications and variations may be made thereto by those of ordinary skill in the art without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to be limitative of the invention so further described in such appended claims.

What is claimed is:

1. A real-time method of deriving composition information regarding a moving web in a manufacturing environment, said method comprising steps of:
   (a) providing a photodetector assembly having a plurality of photodetectors at respective detection locations across the transverse direction of said moving web;
   (b) illuminating said moving web so as to provide electromagnetic energy at each of said photodetectors;
   (c) measuring electromagnetic energy at each of said detection locations;
   (d) deriving said composition information for each of said detection locations based on absorbance of said electromagnetic energy thereat; and
   (e) controlling application of a predetermined add-on component to said moving web based on said composition information, said add-on component contributing selected characteristics to the web.

2. A method as set forth in claim 1, wherein application of said predetermined component is controlled automatically based on said composition information.

3. A method as set forth in claim 1, further comprising the step of presenting a graphical display to a human operator, said graphical display showing quantitative levels of said predetermined component in a cross direction of said moving web.

4. A method as set forth in claim 3, wherein application of said predetermined component is manually controlled by said human operator.

5. A method as set forth in claim 1, further comprising the step of presenting a graphical display to a human operator, said graphical display showing quantitative levels of said predetermined component in a cross direction of said moving web.

6. A method as set forth in claim 5, wherein said graphical display illustrates said quantitative levels correlated to a two-dimensional representation of said moving web.

7. A method as set forth in claim 5, wherein said graphical display illustrates said quantitative levels correlated to a three-dimensional representation of said moving web.

8. A method as set forth in claim 5, wherein said graphical display further shows quantitative levels in a machine direction of said moving web.

9. A method as set forth in claim 1, wherein said moving web is a web of tissue paper and said predetermined component is a lotion substance being added to said moving web.

10. A method as set forth in claim 1, wherein step (c) involves detecting a plurality of frequencies at each of said detection locations in order to provide an absorbance spectrum for said predetermined component.

11. A method as set forth in claim 1, wherein component information is simultaneously derived regarding a plurality predetermined components of said moving web.

12. A method as set forth in claim 1, wherein said electromagnetic energy is reflected to said photodetectors from an incident source located on a same side of said moving web.

13. A method as set forth in claim 1, wherein said electromagnetic energy is transmitted to said photodetectors from an incident source located on an opposite side of said moving web.

14. An apparatus for deriving composition information regarding at least one predetermined component of a moving web, said apparatus comprising:
- a plurality of radiation sources adapted to illuminate said moving web with electromagnetic energy in at least two predetermined frequency bands;
- a photodetector assembly having a plurality of photodetectors spaced apart from said moving web for detecting levels of said electromagnetic energy in respective of said frequency bands, said photodetector assembly being operative to detect levels of said electromagnetic energy at multiple detection locations across the transverse direction of said moving web; and
- processor means in electrical communication with said photodetector assembly, said processor means operative to derive said composition information for each of said detection locations based on absorbance of said electromagnetic energy thereat.

15. An apparatus as set forth in claim 14, further comprising display means for presenting a graphical display showing quantitative levels of said predetermined component in a cross direction of said moving web.

16. An apparatus as set forth in claim 15, wherein said display means is operative to present said quantitative levels correlated to a two-dimensional representation of said moving web.

17. An apparatus as set forth in claim 15, wherein said display means is operative to present said quantitative levels correlated to a three-dimensional representation of said moving web.

18. An apparatus as set forth in claim 15, wherein said display means further shows quantitative levels in a machine direction of said moving web.

19. An apparatus as set forth in claim 15, wherein said plurality of radiation sources are situated on a same side of said moving web as said photodetector assembly.

20. An apparatus as set forth in claim 19, wherein said plurality of radiation sources are situated on an opposite side of said moving web from said photodetector assembly.

21. A real-time method of deriving composition information regarding at least one predetermined component added to a moving web of tissue paper in a manufacturing environment, said method comprising steps of:
(a) illuminating said moving web with electromagnetic energy in at least two predetermined frequency bands;
(b) measuring said electromagnetic energy as diffused by said moving web at each of a plurality of detection locations across a transverse direction of said moving web;
(c) deriving said composition information for each of said detection locations based on absorbance of said electromagnetic energy thereat; and
(d) controlling application of said predetermined component to said moving web based on said composition information.

22. A method as set forth in claim 21, wherein application of said predetermined component is controlled automatically based on said composition information.

23. A method as set forth in claim 21, further comprising the step of presenting a graphical display to a human operator, said graphical display showing quantitative levels of said predetermined component in a cross direction of said moving web.

24. A method as set forth in claim 23, wherein application of said predetermined component is manually controlled by said human operator.

25. A method as set forth in claim 21, further comprising the step of presenting a graphical display to a human operator, said graphical display showing quantitative levels of said predetermined component in a cross direction of said moving web.

26. A method as set forth in claim 25, wherein said graphical display illustrates said quantitative levels correlated to a two-dimensional representation of said moving web.

27. A method as set forth in claim 25, wherein said graphical display illustrates said quantitative levels correlated to a three-dimensional representation of said moving web.

28. A method as set forth in claim 26, wherein said graphical display further shows quantitative levels in a machine direction of said moving web.

29. A method as set forth in claim 21, wherein said predetermined component is a lotion substance being added to said moving web.

30. A method as set forth in claim 29, wherein said composition information is derived by detecting a major constituent of said lotion substance.

31. A real-time method of deriving composition information regarding at least one predetermined component added to a moving web, said method comprising steps of:
(a) illuminating said moving web with electromagnetic energy;
(b) at each of a plurality of detection locations across a transverse direction of said moving web, measuring said electromagnetic energy in a plurality of frequency bands falling within a frequency range of 0.2–200 microns;
(c) combining spectral information at each of said frequency bands into a supervector; and
(d) processing said supervector using multivariate mathematical techniques to produce a spatial data matrix of said composition information correlated to said detection locations.

32. A method as set forth in claim 31, further comprising the step of producing a composition map of said predetermined component from said spatial data matrix.

33. A method as set forth in claim 31, further comprising the step of producing a simple quality value for said predetermined component from said spatial data matrix.

* * * * *